United States Patent
Johansson et al.

(10) Patent No.: US 8,668,338 B2
(45) Date of Patent: Mar. 11, 2014

(54) SYSTEMS AND METHODS FOR REFRACTIVE CORRECTION IN VISUAL FIELD TESTING

(75) Inventors: Göran Anders Johansson, San Francisco, CA (US); Matthew J. Everett, Livermore, CA (US); Christopher J. R. V. Baker, Moraga, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 22 days.

(21) Appl. No.: 13/422,935

(22) Filed: Mar. 16, 2012

(65) Prior Publication Data

US 2013/0070204 A1   Mar. 21, 2013

Related U.S. Application Data

(60) Provisional application No. 61/453,860, filed on Mar. 17, 2011.

(51) Int. Cl.
*A61B 3/02* (2006.01)

(52) U.S. Cl.
USPC .......................................... 351/224

(58) Field of Classification Search
USPC ................................. 351/223–228
See application file for complete search history.

(56) References Cited

U.S. PATENT DOCUMENTS

| | | |
|---|---|---|
| 3,305,294 A | 2/1967 | Alvarez |
| 3,891,311 A | 6/1975 | Fletcher et al. |
| 5,024,519 A | 6/1991 | Howard et al. |
| 5,104,214 A | 4/1992 | Sims |
| 5,138,494 A | 8/1992 | Kurtin |
| 5,220,361 A | 6/1993 | Lehmer et al. |
| 5,323,194 A | 6/1994 | Campbell et al. |
| 5,459,536 A | 10/1995 | Shalon et al. |
| 5,491,757 A | 2/1996 | Lehmer et al. |
| 5,668,620 A | 9/1997 | Kurtin et al. |
| 5,956,183 A | 9/1999 | Epstein et al. |
| 6,040,947 A | 3/2000 | Kurtin et al. |
| 6,053,610 A | 4/2000 | Kurtin et al. |
| 6,069,742 A | 5/2000 | Silver |

(Continued)

FOREIGN PATENT DOCUMENTS

CN   201481388 U   5/2010

OTHER PUBLICATIONS

International Search Report and Written Opinion received for PCT Patent Application No. PCT/EP2012/054586, mailed on Jun. 6, 2012, 10 pages.

(Continued)

*Primary Examiner* — Scott J Sugarman
*Assistant Examiner* — Mustak Choudhury
(74) *Attorney, Agent, or Firm* — Morrison & Foerster LLP

(57) ABSTRACT

Systems and methods for providing variable refractive correction in a visual field testing device are presented. One embodiment of the variable refractive correction involves two or more aligned transmissive plates arranged to produce changes in refractive power by translation or rotation of the plates relative to each other. Several alternative designs for providing variable refractive correction are described. The refractive correction can be set manually or automatically based on knowledge of the refractive error of a specific patient and spherical and cylindrical refractive correction are possible. Additional lens systems can be used to extend the range of refractive correction to accommodate a larger patient population.

22 Claims, 2 Drawing Sheets

(56) References Cited

U.S. PATENT DOCUMENTS

| | | |
|---|---|---|
| 6,309,068 B1 | 10/2001 | Kohayakawa |
| 6,369,954 B1 | 4/2002 | Berge et al. |
| 6,618,208 B1 | 9/2003 | Silver |
| 7,008,054 B1 | 3/2006 | Kurtin et al. |
| 7,393,099 B2 | 7/2008 | Koops et al. |
| 7,423,811 B2 | 9/2008 | Silver |
| 7,438,416 B2 | 10/2008 | Hayashi et al. |
| 7,553,020 B2 | 6/2009 | Goldfain et al. |
| 7,594,726 B2 | 9/2009 | Silver |
| 7,768,712 B2 | 8/2010 | Silver et al. |
| 7,789,013 B2 | 9/2010 | Silver |
| 7,826,146 B2 | 11/2010 | Campbell |
| 7,841,715 B1 | 11/2010 | Morrison |
| 2004/0021919 A1 | 2/2004 | Lee |
| 2004/0100617 A1* | 5/2004 | Abitbol ............... 351/205 |
| 2006/0001831 A1* | 1/2006 | Sumiya ............... 351/224 |
| 2006/0077562 A1 | 4/2006 | Silver |
| 2006/0170864 A1 | 8/2006 | Kuiper et al. |
| 2006/0250699 A1 | 11/2006 | Silver |
| 2008/0007689 A1 | 1/2008 | Silver |
| 2008/0008600 A1 | 1/2008 | Silver |
| 2009/0213471 A1 | 8/2009 | Silver et al. |
| 2010/0045930 A1 | 2/2010 | Silver et al. |
| 2010/0053543 A1 | 3/2010 | Silver et al. |
| 2010/0265463 A1* | 10/2010 | Lai ............... 351/237 |

OTHER PUBLICATIONS

Asatryan et al., "Optical Lens with Electrically Variable Focus using an Optically Hidden Dielectric Structure", Optics Express, vol. 18, No. 13, Jun. 21, 2010, pp. 13981-13992.

Barbero, Sergio, "The Alvarez and Lohman Refractive Lenses Revisited", Optics Express, vol. 17, No. 11, May 25, 2009, pp. 9376-9390.

Barton et al., "Diffractive Alvarez Lens", Optics Letters, vol. 25, No. 1, Jan. 1, 2000, pp. 1-3.

Cheng et al., "Adaptive Mechanical-Wetting Lens Actuated by Ferrofluids", Optics Communications, vol. 284, 2011, pp. 2118-2121.

Douali et al., "Self-Optimized Vision Correction with Adaptive Spectacle Lenses in Developing Countries", Ophthalmic and Physiological Optics, vol. 24, 2004, pp. 234-241.

Holochip—Products APX 1007, "Technology Overview: Technical and White Papers Patents", retrieved from Internet on Jul. 16, 2012, 1 page, available at: www.holochip.com/technologyt/overview.html.

Hongbin et al., "Optofluidic Variable Aperture", Optics Letters, vol. 33, No. 6, Mar. 15, 2008, pp. 548-550.

Marks et al., "Adjustable adaptive Compact Fluidic Phoropter with no Mechanical Translation of Lenses", Optics Letters, vol. 35, No. 5, Mar. 1, 2010, pp. 739-741.

Marks et al., "Adjustable Fluidic Lenses for Ophthalmic Corrections", Optics Letters, vol. 34, No. 4, Feb. 15, 2009, pp. 515-517.

Marks et al., "Astigmatism and Defocus Wavefront Correction via Zernike Modes Produced with Fluidic Lenses", Applied Optics, vol. 48, No. 19, Jul. 1, 2009, pp. 3580-3587.

Murali et al., "Three-Dimensional Adaptive Microscopy using Embedded Liquid Lens", Optics Letters, vol. 34, No. 2, Jan. 15, 2009, pp. 145-147.

Ren et al., "Tunable-Focus Liquid Lens Controlled using a Servo Motor", Optics Express, vol. 14, No. 18, Sep. 4, 2006, pp. 8031-8036.

Ren et al., "Variable-Focus Liquid Lens by Changing Aperture", Applied Physics Letters, vol. 86, 2005, pp. 211107-1-211107-3.

Son et al., "Tunable-Focus Liquid Lens System Controlled by Antagonistic Winding-Type SMA Actuator", Optics Express, vol. 17, No. 16, Aug. 3, 2009, pp. 14339-14350.

* cited by examiner

SYSTEMS AND METHODS FOR REFRACTIVE CORRECTION IN VISUAL FIELD TESTING

CROSS-REFERENCE TO RELATED APPLICATIONS

This application claims priority to U.S. Provisional Application Ser. No. 61/453,860, filed Mar. 17, 2011, the entire disclosure of which is incorporated by reference.

TECHNICAL FIELD

Various embodiments of the present invention relate generally to the field of visual field testing. In particular, the invention is directed towards an improved means of correcting the refractive error in a perimeter or other visual field testing device to increase the reliability of the visual field test, improve the ease of use of the instrument, and improve patient comfort

BACKGROUND OF THE INVENTION

To achieve a reliable result on a visual field test it is important to correct the patient's refractive error, since refractive blur will reduce the visual sensitivity to perimetric stimuli. Today, it is standard practice to reduce the refractive error to within 1 diopter, which would produce less than one decibel of depression of the hill of vision when testing with a Goldmann size II stimulus (see for example Anderson D. R et al Automated Static Perimetry Second Edition 1999: Mosby Inc.) The use of a set of standard ophthalmic trial lenses is the commonly used method of correcting a patient's refractive error. The perimetry operator selects and inserts lenses into the line of vision of the patient based on a previously determined refractive value for the patient. A large fraction of all patients require such correction due to myopia, hyperopia or presbyopia. Although a set of trial lenses are available in most clinical settings, they provide a cumbersome and time consuming method of reducing refractive blur during a visual field test.

There are also a number of negatives associated with trial lenses leading to reduced reliability of the visual field test. Trial lens "rim artifact", where the trial lens frame blocks parts of the visual filed, can be confused by inexperienced clinicians as actual field loss. Mistakes in selecting the correct trial lens can cause a general depression of the visual field. Furthermore, the patient's comfort is often reduced by the use of trial lenses and overall workflow in the office setting is significantly slowed down.

It is therefore a general objective of this invention to provide both a method and an apparatus to improve the reliability of the visual field test, improve patient comfort, and reduce errors and possible mistakes associated with the use of trial lenses. Furthermore, the invention will improve workflow and the throughput of the clinics.

BRIEF SUMMARY OF THE INVENTION

The invention includes a system for correcting a patient's refractive error and is used in combination with an apparatus, e.g., a perimeter, which measures a patient's response to a stimulus presented in the patient's visual field. The system includes variable refractive correction optics used in conjunction with a perimeter system. The refractive power of the lens device is adjustable in a manner to correct a patient's refractive error and provide the patient with a sharp image of a visual stimulus within the tested area of the patient's visual field.

Furthermore, the invention includes a method to acquire or retrieve the patient's refractive status from the instrument, the instrument operator or automatically from an EMR or other patient database. The method also includes a means to calculate the patient's refractive error and a means to calculate the refractive power necessary to cancel out said refractive error and a means to automatically adjust the lens device to the required refractive power.

DETAILED DESCRIPTION OF THE INVENTION

As described above, the use of a set of trial lenses has significant disadvantages for correcting a patient's refractive error during visual field testing. The invention described herein includes a system for correcting a patient's refractive error used in combination with a visual field testing instrument. An example of one such visual field testing instrument is the HFA sold by Carl Zeiss Meditec (Dublin, Calif.) and described in U.S. Pat. No. 5,323,194 hereby incorporated by reference. The HFA is the gold standard for visual field testing and consists of a semi-hemispherical "bowl" that light patterns can be projected onto. A patient's perception of these test stimuli over a range of locations is analyzed while the patient's gaze is fixed on a single location. The variable refractive correction system could also be applied to other types of perimeters, e.g. direct projection perimeters, or other devices capable of measuring visual field or visual function.

Figure 1:
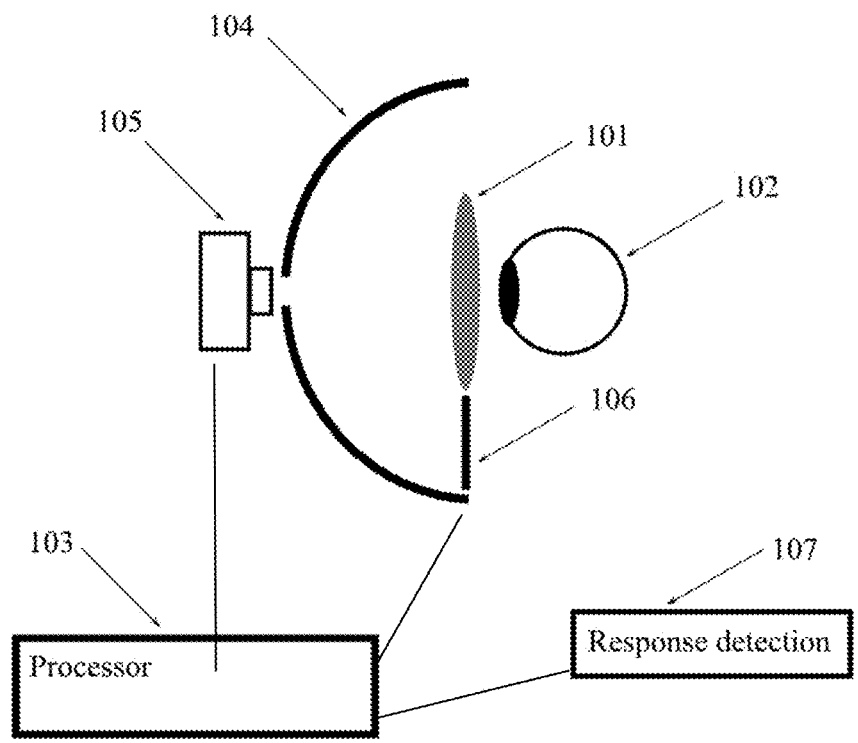
FIG. 1 shows a block diagram of one embodiment of the present invention.

In a preferred embodiment, the variable refractive correction optics are attached to the front of the perimeter in either a fixed or removable fashion, but it could also be built into the perimeter itself. In either case, the lens device providing the variable refractive correction could be removed when the central region of the visual field is not being tested, to allow for testing in other regions of the visual field. In the most basic sense, the invention incorporates a lens device with a means to vary its refractive power combined with a visual field testing device as shown in FIG. 1. The instrument consists of a display surface or device, in this case a bowl 104 for projection of visual field test images, a camera 105 for collecting information on the position and gaze of the eye (e.g. vertex location, pupil location and gaze direction), a variable refractive correction optics 101 attached to the perimeter through holder 106, positioned in between the eye of a patient 102 and the perimeter, and a response detection system 107 for measuring the patient's perception of the various stimuli. A processor 103 interfaces with the device for analyzing the test results, controlling the variable refractive correction optics in the case of automated adjustment, and for interfacing with the camera among other functions. The display device could be curved or flat, and the stimuli could be displayed in any number of arrangements including forward projection, back projection, or direct illumination of light sources (LEDs, OLEDs, etc). The response detection system could be a button pressed by a patient or a means for recording an audible response of the patient among others.

A variety of different embodiments of the variable refractive correction optics can be imagined. Below we describe three embodiments. It will be obvious to one skilled in the art to envision others that would fall into the scope of this invention.

Adjustable Set of Trial Lenses

Figure 2:
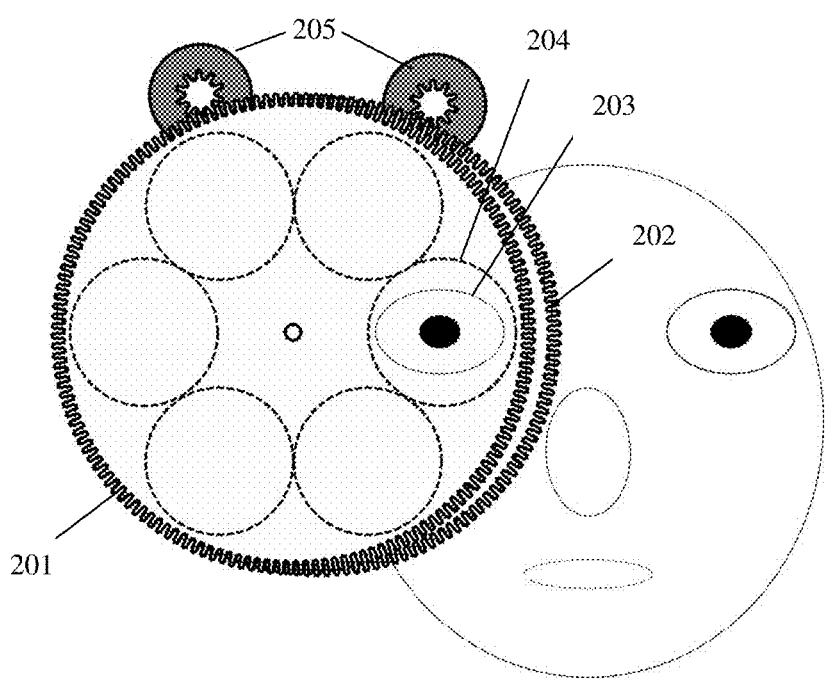
FIG. 2 displays an embodiment of the variable refractive correction using rotatable wheels containing trial lenses of various refractive powers.

In one embodiment of the present invention, the variable refractive correction optics can be realized by combining one or more sets of trial lenses in an easily adjustable fashion such as a rotating wheel or multiple wheels, which can easily be integrated into the visual field testing instrument. To achieve a broad enough range of refractive correction with fine enough adjustment steps, two or more lens wheels are preferable. By combining one lens 204 from a selected set of trial lenses mounted in one wheel type arrangement 201 with a second lens (not shown) from a second set of trial lenses mounted on a second wheel type arrangement 202 as illustrated schematically in FIG. 2 in front of the eye of the patient 203, a large number of refractive powers can be achieved. For example, 36 different values are possible if each wheel has six lenses. Values from −10.5 D to +7 with 0.5 D steps can be implemented if wheel one has values: −1.5, −1, −0.5, 0, +0.5, +1 D and wheel two has −9, −6, −3, 0, +3, +6 D. This example includes two separate sets of lenses but can easily be extended to more sets of lenses. Another advantage of combining lens elements in this fashion to cover a large refractive power range is that such a device occupies very little space in the axial direction.

The set of trial lenses could be mounted in an injection molded plastic wheel that houses the lenses, bearing, and gears or similar mechanism for rotating the wheel. By moving the lenses further from the rotation center, conflicts between facial features and the lens system can be reduced. Alternatively, the trial lenses can be placed on a belt to move the non-used lenses further away from the patient. Other embodiments can be easily envisioned by someone skilled in the art. The lenses can be rotated to position manually, or by means of motors 205 to provide automatic refraction correction for the patient.

Figure 3:
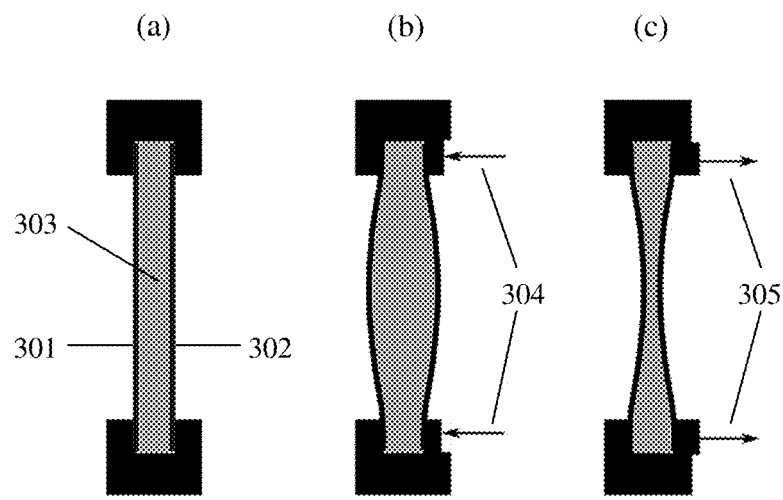
FIG. 3 illustrates a liquid-lens that could be used in one embodiment of the present invention.

This method of using mounted sets of trial lenses configured in an adjustable manner is significantly different from that described in U.S. Pat. No. 5,024,519 wherein a single lens is translated along the optical axis to compensate for refractive errors Liquid Lens In a second embodiment of the lens system illustrated in FIG. 3, a liquid lens is utilized to provide a variable refractive correction. A liquid lens typically consists of one or two transparent and flexible membranes 301 and 302, encapsulating a volume of liquid 303 with a specific refractive index. A variety of liquid lenses have been described in the literature. Continuously adjustable refractive positive or negative powers of up to 25-50 diopters have been demonstrated [see for example http://www.holochip.com and Ren et. al "Variable-focus liquid lens by changing aperture" Applied Physics Letters 86:21107 2005 hereby incorporated by reference]. An actuator changes the distribution of the volume of the liquid, to adjust the refractive power of the lens as shown pictorially in FIGS. 3(b) and 3(c) creating convex and concave lenses respectively. In this case pressure is applied or released to the periphery of the lens as indicated by arrows 304 and 305. The volume change can be accomplished either manually or automatically by the instrument, by tuning the radius of an annular sealing ring, or by squeezing or releasing the periphery of the lens or other method which changes the profile of the lens or volume of the liquid. A liquid lens for perimetry would typically have 36 mm clear aperture to ensure the patient can be tested within ±30° visual field. The range would typically be from −10 to +10 diopter, but could be, e.g., offset with lenses to target high myopic or hyperopic populations. A liquid lens can also be used to provide cylindrical correction.

Alvarez Lens

Figure 4:
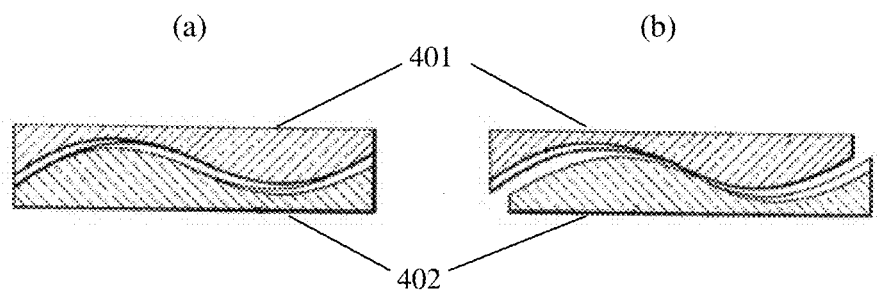
FIG. 4 illustrates an Alvarez lens system that could be used in one embodiment of the present invention.

In a third embodiment of a variable lens system two or more transmissive plates of different shapes are translated perpendicular to the optical axis or rotated around the axis to produce a change in refractive power. One example of such a system is an Alvarez lens system. This lens system, invented by Luis W. Alvarez in the 1960s (see U.S. Pat. No. 3,305,294 hereby incorporated by reference) and illustrated in FIG. 4, consists of two transmissive plates 401 and 402, where each plate has a flat surface and a surface shaped in a specific two-dimensional polynomial shape. Parallel translation of the two plates relative to each other produces a change in refractive power, e.g., spherical and/or cylindrical as illustrated in FIGS. 4(a) and (b). Various embodiments of lens systems incorporating the general principle of shifting or rotating transmissive plates relative to each other to create variations in spherical and cylindrical power would be known by those skilled in the art. Instead of or in addition of smooth refractive surfaces, the transmissive plates could also have diffractive or Fresnel surfaces.

Until recently, it has been difficult and expensive to manufacture Alvarez type lenses, but recent development in lens design and injection molding technologies have solved most of the issues. It would be advantageous to use an Alvarez type lens with automatic adjustment to correct refractive error during a perimetry test. The refractive power of the lens is easily adjusted with a small motorized translation stage, shifting one transmissive plate relative to the other. If the plates are moved in an orthogonal direction to that described above they can produce a variable cylindrical lens. A pair of these variable cylindrical lenses, disposed at 90 degrees to each other, can be used to provide the cylindrical power and angle required to correct a patient's astigmatism. Hence the patient's astigmatic correction can be automatically provided by a pair of motors, each shifting one transmissive plate relative to the other in the two orthogonal axes.

Additional technologies to provide variable refractive correction within a perimetry system could include using lenses based on liquid crystal, ferrofluid, holograms, or electrowetting (see for example Cheng, H.-C. et al Adaptive mechanical-wetting lens actuated by ferrofluids Optics Communications, 284(8): 2118-2121 2011 and US Patent Publication No. 2004/0021919.)

Extending the Range of Refractive Error Correction

Many of the above implementations would automatically correct the refractive error for a very large fraction of the perimetry patient population. However, it would be advantageous to extend the range of refractive correction to cover virtually all patients. This can be accomplished by a semi-automatic method of adding a static auxiliary lens to offset the power of the variable refractive correction optics, e.g., by adding a −10 D or a +10 D to a ±10 D liquid lens, the total range can be −20 D to +20 D with a step size of less than 0.25 D. Covering the same range with discreet trial lenses in 0.25 D steps would require 160 lenses, while the present innovation only requires the variable refractive correction optics and two additional lenses.

Furthermore, a small fraction of perimetry patients require cylindrical refractive correction in addition to spherical correction, which can also be added to the variable lens system by an auxiliary lens. Consequently, combining a variable lens system with 5-8 add-on lenses to provide additional spherical and cylindrical power, can correct refractive errors for virtually all perimetry patients. This is a great advantage and cost saving over present systems which uses hundreds of discreet trial lens for the refractive correction of patients.

The auxiliary lens could be attached to the variable refractive correction optics by mechanical or magnetic means to allow it to quickly be positioned, replaced or removed from the variable refractive correction optics. As stated before, mistakes are sometimes made in selecting a trial lens and although this innovation would significantly reduce the number of trial lenses and possibilities of selecting the wrong one, it would be advantageous to automatically identify which lens and lens power have been selected and placed in addition to the variable lens and notify the operator if the wrong lens has been selected. The auxiliary lens would therefore preferably be equipped with means to identify itself to the perimetry system when it is placed in its holder through, e.g., mechanical, magnetic, electrical, optical or other means know to someone skilled in the art. For example, a camera such as the IR camera used for gaze tracking in the current HFA perimeter (reference sign 105 in FIG. 1 and described in U.S. Pat. Nos. 5,220,361 and 5,491,757 hereby incorporated by reference) could by image processing identify markings placed on the auxiliary lens or its rim and determine which lens has been placed and if it is the appropriate lens for the specific patient undergoing the perimetry test. The markings, if on the actual lens surface, would typically only be seen by the camera and would be transparent to visible light, thereby not affecting the patient's field test by obscuring the field of view. Furthermore, not only could the type and power of the lens be identified by markings on the lens or its rim, but it would also be advantageous to identify with said marking if a cylindrical auxiliary lens has been placed with a correct angular orientation corresponding to the selected patient's refractive error. The angle of the cylindrical lens can be set manually using further visible markings on the periphery, or can be set manually using feedback from the markings provided by the camera or the angle can be adjusted automatically by motors, using feedback from an angle measurement device or from the markings.

Another method of creating a variable power cylindrical lens is to use a Stokes Cell. This consists of two cylindrical lenses of equal and opposite power. When placed one on top of the other with their cylindrical axes parallel they will cancel and the lens will have no cylindrical power. When one lens is rotated relative to the other such that their cylindrical axes are at 90 degrees they will create maximum cylindrical power at an axis midway between the two axes. In this way the number of lenses required to correct astigmatism can be reduced to two. Using visible markings the power of the lens can be preset by rotating the lenses relative to each other out of the instrument and the lens can then be applied to the spherical lens or the trial lens holder, using visible markings to define the correct axis. In another embodiment the lenses are pre-attached to the spherical lens or the trial lens holder and are rotated using feedback from the camera. In this instance the position of each lens is computed by the instrument and the operator only has to rotate each lens according to feedback provided on the screen. If the screen is not conveniently visible during this process further feedback can be provided, either in the form of a second auxiliary screen, information projected on the bowl or audible information in the form of instructions, variable frequency, variable amplitude or any other means familiar to those skilled in the art. In another embodiment the two lenses are motorized, using the feedback from the camera, to provide the correct angle of each lens to satisfy the computed lens positions. Each lens could be motorized individually or a single motor could be used to move both lenses.

In all cases the information from the markings can be used to ensure that the patient has the appropriate sphere, cylinder and axis refractive correction. Any lens that is either incorrect or incorrectly positioned according to predefined tolerance bands will cause a warning to the operator. The warning signifies operator error in the case of manual refractive devices or system failure in the case of automatic devices In another embodiment of the present invention, two or more of the above described variable refractive correction optical systems can be combined to extend the range or precision of the refractive correction, e.g., the Alvarez lens could be combined with a set of trial lenses placed on a lens wheel or belt to cover a wider range of refractive power. Those skilled in the art could easily combine any of the above described systems to extend the refractive power range and/or increase refractive power resolution.

Refractive Error Data Handling

Today, most patients' refractive statuses reside in one or more patient databases and typically include the spherical and cylindrical parts of the refractive error and the angular orientation of the cylindrical part for both eyes of a patient. It would be advantageous to let the perimetry system automatically measure the refractive error for the patient to be tested, using an auto-refracting technique known to those skilled in the art, or retrieve it, by network or other means, from the patient database or record system. Alternatively, the operator can manually provide the perimeter with the refractive error values if the patient record is only available on paper. With the knowledge of the patient's refractive status, the instrument can then calculate the spherical equivalent power of the spherical lens(es) necessary to provide the patient with a well focused view of the perimetric stimulus. The system can use an actuator, e.g., an electrical motor, to adjust the lens system to the correct power. It would be desirable to use a feedback system to ensure that the automatic spherical lens has the correct power and stays in calibration. If the instrument finds that the patient's refractive error is outside the range of the variable refractive correction optics, the instrument can instruct the operator to add an additional refractive lens of specified power to the system to achieve the desired total power. This could also include adding cylindrical power to the system. The above described procedure would save a significant amount of time and reduce the risk of errors associated with preparing a patient for a visual field test.

If the refractive status of the patient is not known either by auto-refractive measurement or patient record or database, it could also be very advantageous to let the perimeter instrument use the variable refraction correction optics to determine the refractive error of the patient. For example, a Snellen like chart for visual acuity could be projected inside the perimetry bowl and the lens system for variable refraction error correction could be adjusted either by the perimeter or the operator until the patient can view the Snellen chart clearly. For someone skilled in the art, it would be obvious to use other methods to find the refractive error of the patient, e.g., by detecting light reflected off a patient's retina and performing a nulling operation with the variable refractive correction optics.

Lens Alignment Relative to Patient

An additional aspect of the invention is the ability of the variable refractive correction to physically move in line with the patient separate from the overall instrument. As previously mentioned, a few ophthalmic instruments, e.g., perimeters and phoropters, use trial lenses for refractive correction during examinations. Mounting a trial lens statically to the instrument is problematic in that the patient's head could move over the course of the test causing the eye to move outside the clear aperture of the lens or too far back from the lens. This leads to erroneous test results and is especially problematic for long tests. One way to avoid this is to ensure that the eye is always appropriately located relative to the trial lens. This has been accomplished by either moving the head of the patient based on guidance from a pupil tracker or by moving the entire instrument to maintain alignment. Both of these methods are problematic. If moving the patient's head, the movement must be slow or else risks disturbing the concentration of the patient during the test. Furthermore, often the patient does not follow the movement of the chin/head rest or moves in a different direction. Moving the entire instrument to maintain alignment is often costly and difficult due to instrument weight.

Here, we suggest to detect the patient's eye position relative to the lens system and, if there is any significant deviation due to head motion, only the lens system is moved to recenter on the eye position. The eye position relative to the lens system could be provided by analyzing images of the pupil collected by the camera 105 shown in FIG. 1. An additional camera within the device could also be provided for this purpose and be used to collect pupil images or images of the optics relative to a different facial feature. Additional ways to provide location information of the eye relative to the lens could include measuring the position of variable refractive correction optics themselves using either a camera or some position tracking while ensuring that the patient's eye is aligned to the lens. The position of the variable refractive correction optics 101 relative to the patient could be moved by a motor connected to the optics holder 106 based on information and controlling commands sent by the processor 103. This aspect of the invention could be applied to the variable refractive lens system or in general to any trial lens used in combination with a visual field tester. There are several significant advantages to moving the lens system independent from the overall instrument. The trial lens and its holder have very little inertia so can be moved fast and with high precision, the patient is not disturbed by a moving head/chin rest and can fully concentrate on the exam, and the system is not dependent on the patient trying to follow the motion of the head/chin rest.

Although various embodiments that incorporate the teachings of the present invention have been shown and described in detail herein, those skilled in the art can readily devise many other varied embodiments that still incorporate these teachings.

The following references are hereby incorporated by reference:

U.S. Patent Documents
U.S. Pat. No. 3,305,294
U.S. Pat. No. 5,024,519
U.S. Pat. No. 5,104,214
U.S. Pat. No. 5,138,494
U.S. Pat. No. 5,220,361
U.S. Pat. No. 5,323,194
U.S. Pat. No. 5,491,757
U.S. Pat. No. 5,668,620
U.S. Pat. No. 5,956,183
U.S. Pat. No. 6,040,947
U.S. Pat. No. 6,053,610
U.S. Pat. No. 6,069,742
U.S. Pat. No. 6,369,954
U.S. Pat. No. 6,618,208
U.S. Pat. No. 7,008,054
U.S. Pat. No. 7,393,099
U.S. Pat. No. 7,423,811
U.S. Pat. No. 7,553,020
U.S. Pat. No. 7,594,726
U.S. Pat. No. 7,768,712
U.S. Pat. No. 7,789,013
U.S. Pat. No. 7,826,146
U.S. Pat. No. 7,841,715
Publication No. 2004/0021919
Publication No. 2006/0077562
Publication No. 2006/0250699
Publication No. 2008/0007689
Publication No. 2008/0008600
Publication No. 2009/0213471
Publication No. 2010/0045930
Publication No. 2010/0053543

Non-Patent References http://www.holochip.com

Anderson D. R et al Automated Static Perimetry Second Edition 1999: Mosby Inc.

Asatryan, K et al "Optical lens with electrically variable focus using an optically hidden dielectric structure" Optics Express 18(13): 13981-13992 2010.

Barbero, S. "The Alvarez and Lohman refractive lenses revisited" Optics Express 17(11):9376-9390 2009.

Barton, I. M et al "Diffractive Alvarez lens" Optics Letters 25(1):1-3 2000.

Cheng, H.-C. et al "Adaptive mechanical-wetting lens actuated by ferrofluids" *Optics Communications,* 284(8): 2118-2121 2011

Douali M. G. et al "Self-optimized vision correction with adaptive spectacle lenses in developing countries" Ophth. Phsiol. Opt. 24: 234-241 2004.

Hongbin, Y et al "Optofluidic variable aperture" Optics Letters 33(6): 548-550 2008.

Marks, R et al "Adjustable fluidic lenses for ophthalmic corrections" Optics Letters 34(4) 515-517 2009.

Marks, R et al "Astigmatism and defocus wavefront correction via Zernike modes produced with fluidic lenses" Applied Optics 48(19): 3580-3587 2009.

Marks, R et al "Adjustable adaptive compact fluidic phoropter with no mechanical translation of lenses" Optics Letters 35(5) 739-741 2010.

Murali, S et al "Three-dimensional adaptive microscopy using embedded liquid lens" Optics Letters 34(2): 145-147 2009.

Ren et al "Tunable-focus liquid lens controlled using a servo motor" Optics Express 14(18): 8031-8036 2006.

Ren et. al "Variable-focus liquid lens by changing aperture" Applied Physics Letters 86:21107 2005

Son, H. M et al "Tunable-focus liquid lens system controlled by antagonistic winding-type SMA actuator" Optics Express 17(16): 14339-14350 2009.

What is claimed is:

1. An apparatus for analyzing the visual field of a patient, said apparatus comprising:
  a display surface;
  a visual stimulus system that generates stimuli at various locations on the display surface;
  a response detection system for collecting data on the patient's perception of the visual stimuli;
  variable refractive correction optics operably attached to said apparatus for correcting the refractive error of the patient; and a processor operatively connected to the variable refractive correction optics, said processor for receiving a refractive error value of the patient and in response automatically adjusting the variable refractive correction optics to compensate for the refractive error of the patient.

2. An apparatus as recited in claim 1, wherein the variable refractive correction optics include a liquid lens.

3. An apparatus as recited in claim 1, wherein the variable refractive correction optics include two or more aligned transmissive plates arranged to produce changes in refractive power by translation or rotation of the plates relative to each other.

4. An apparatus as recited in claim 1, wherein the variable refractive correction optics include a pair of aligned rotatable wheels, each wheel carrying a plurality of lenses having different diopter values.

5. An apparatus as recited in claim 1, wherein the variable refractive correction optics provide a range of refractive correction extending from approximately −10 to approximately +10 diopters.

6. An apparatus as recited in claim 1, further comprising one or more auxiliary lenses to extend the range of the refractive correction.

7. An apparatus as recited in claim 6, wherein the variable refractive correction optics combined with the auxiliary lens provide a range of refractive correction extending from approximately −20 to approximately +20 diopters.

8. An apparatus as recited in claim 6, wherein the auxiliary lens provides spherical refractive correction.

9. An apparatus as recited in claim 6, wherein the auxiliary lens provides cylindrical refractive correction.

10. An apparatus as recited in claim 9, wherein the auxiliary lens is a Stokes cell.

11. An apparatus as recited in claim 6, further comprising identification means for determining one or both of the presence and the orientation of the auxiliary lens.

12. An apparatus as recited in claim 1, further comprising a feedback system to ensure the correct refractive correction has been set by the apparatus.

13. An apparatus as recited in claim 1, further comprising a means for monitoring the location of the eye relative to the variable refractive correction optics and a motorized adjustment to reposition the optics relative to the eye of the patient without moving the apparatus itself.

14. An apparatus for testing the visual field of a patient, said apparatus comprising:
a display surface;
a visual stimulus system that generates stimuli at various locations on the display surface;
a response detection system for collecting data on the patient's perception of the visual stimuli;
means operably attached to the apparatus for providing a continuously variable refractive correction of the patient;
an actuator coupled to said refraction correction means to adjust the refractive power; and
a processor operatively connected to the actuator, said processor for receiving a refractive error value of the patient and in response automatically adjusting the refraction correction to compensate for the refractive error of the patient.

15. An apparatus as recited in claim 14, further comprising one or more auxiliary lenses to extend the range of the refractive correction.

16. An apparatus as recited in claim 15, wherein the auxiliary lens provides cylindrical refractive correction.

17. An apparatus as recited in claim 15, wherein the auxiliary lens provides spherical refractive correction.

18. An apparatus as recited in claim 15, further comprising identification means for determining one or both of the presence and the orientation of the auxiliary lens.

19. An apparatus as recited in claim 14, further comprising a feedback system to ensure the correct refractive correction has been set by the apparatus.

20. An apparatus as recited in claim 14, further comprising a means for monitoring the location of the eye relative to the variable refractive correction optics and a motorized adjustment to reposition the optics relative to the eye of the patient without moving the apparatus itself.

21. An apparatus as recited in claim 14 wherein said refraction correction means comprises two or more transmissive plates arranged to produce changes in refractive power by translation or rotation of the plates relative to each other.

22. An apparatus as recited in claim 14 wherein said refraction correction means comprises a liquid lens.

* * * * *

UNITED STATES PATENT AND TRADEMARK OFFICE
CERTIFICATE OF CORRECTION

PATENT NO. : 8,668,338 B2
APPLICATION NO. : 13/422935
DATED : March 11, 2014
INVENTOR(S) : Göran Anders Johansson et al.

It is certified that error appears in the above-identified patent and that said Letters Patent is hereby corrected as shown below:

In the Specification

In column 1, line 21, after "comfort" insert -- . --.

In column 3, line 47, after "errors" insert -- . --.

In column 8, line 33, after "2011" insert -- . --.

In column 8, line 53, after "2005" insert -- . --.

Signed and Sealed this
Twenty-fourth Day of June, 2014

Michelle K. Lee
*Deputy Director of the United States Patent and Trademark Office*